US012655084B2

(12) United States Patent
Choi et al.

(10) Patent No.: US 12,655,084 B2
(45) Date of Patent: Jun. 16, 2026

(54) METHOD FOR PREPARING AN ACRYLIC ACID

(71) Applicant: LG Chem, Ltd., Seoul (KR)

(72) Inventors: Inho Choi, Daejeon (KR); Hoiin Jeong, Daejeon (KR); Yong O Im, Daejeon (KR); Jiyoung Lee, Daejeon (KR); Daeho Hong, Daejeon (KR)

(73) Assignee: LG Chem, Ltd., Seoul (KR)

( * ) Notice: Subject to any disclaimer, the term of this patent is extended or adjusted under 35 U.S.C. 154(b) by 548 days.

(21) Appl. No.: 18/032,436

(22) PCT Filed: Nov. 5, 2021

(86) PCT No.: PCT/KR2021/016059

§ 371 (c)(1),
(2) Date: Apr. 18, 2023

(87) PCT Pub. No.: WO2022/103087

PCT Pub. Date: May 19, 2022

(65) Prior Publication Data

US 2023/0391708 A1 Dec. 7, 2023

(30) Foreign Application Priority Data

Nov. 11, 2020 (KR) ........................ 10-2020-0150320
Nov. 4, 2021 (KR) ........................ 10-2021-0150793

(51) Int. Cl.

*C07C 51/377* (2006.01)
*B01J 27/18* (2006.01)
*B01J 35/40* (2024.01)
*B01J 35/55* (2024.01)

(52) U.S. Cl.

CPC ......... *C07C 51/377* (2013.01); *B01J 27/1806* (2013.01); *B01J 35/40* (2024.01); *B01J 35/55* (2024.01)

(58) Field of Classification Search

CPC ....... C07C 51/377; C07C 51/43; C07C 57/04; C07C 59/08; B01J 27/1806; B01J 35/40; B01J 35/55; B01J 27/18

See application file for complete search history.

(56) References Cited

U.S. PATENT DOCUMENTS

| | | | |
|---|---|---|---|
| 2,859,240 | A | 11/1958 | Holmen |
| 4,729,978 | A | 3/1988 | Sawicki |
| 6,998,504 | B1 | 2/2006 | Unverricht et al. |
| 8,772,539 | B2 | 7/2014 | Onda et al. |
| 9,309,180 | B2 | 4/2016 | Kuppinger et al. |
| 9,409,158 | B2 | 8/2016 | Onda et al. |
| 9,611,208 | B2 | 4/2017 | Velasquez et al. |
| 9,714,208 | B2 | 7/2017 | Villalobos et al. |
| 9,890,102 | B1 | 2/2018 | Collias et al. |
| 10,106,481 | B2 | 10/2018 | Velasquez et al. |
| 10,344,108 | B2 | 7/2019 | Godlewski et al. |
| 2002/0052534 | A1 | 5/2002 | Lenglet et al. |
| 2010/0249454 | A1 | 9/2010 | Tanimoto et al. |
| 2012/0277467 | A1 | 11/2012 | Onda et al. |
| 2013/0274094 | A1 | 10/2013 | Velasquez et al. |
| 2013/0274515 | A1* | 10/2013 | Godlewski ........... B01J 27/1806 562/599 |
| 2014/0155653 | A1 | 6/2014 | Dongare et al. |
| 2015/0038735 | A1 | 2/2015 | Ozmeral et al. |
| 2018/0134647 | A1 | 5/2018 | Ozmeral et al. |
| 2018/0258024 | A1 | 9/2018 | Albert et al. |
| 2019/0105651 | A1 | 4/2019 | Velasquez et al. |

FOREIGN PATENT DOCUMENTS

| | | | |
|---|---|---|---|
| CN | 87209610 | U | 5/1988 |
| CN | 1351109 | A | 5/2002 |
| CN | 1454883 | A | 11/2003 |
| CN | 2766951 | Y | 3/2006 |
| CN | 101255109 | A | 9/2008 |
| CN | 102775294 | A | 11/2012 |
| CN | 102513137 | B | 12/2014 |
| CN | 104245761 | A | 12/2014 |
| CN | 106861559 | A | 6/2017 |
| JP | 2007326053 | A | 12/2007 |
| JP | 2011063628 | A | 3/2011 |
| JP | 2014009168 | A | 1/2014 |
| JP | 2014189513 | A | 10/2014 |
| JP | 2014525894 | A | 10/2014 |
| JP | 2015518481 | A | 7/2015 |
| JP | 5902374 | B2 | 4/2016 |
| JP | 2016175840 | A | 10/2016 |
| JP | 6434400 | B2 | 12/2018 |

(Continued)

OTHER PUBLICATIONS

International Search Report for Application No. PCT/KR2021/016059 mailed Mar. 2, 2022, pp. 1-6.
Peng. J. et al., "Barium sulphate catalyzed dehydration of lactic acid to acrylic acid† " Green Chemistry, RSC Publishing, Oct. 2013, pp. 108-111, vol. 16.
Search Report dated Jan. 19, 2026 from the Office Action for Chinese Application No. 202180071136.X issued Jan. 24, 2026, pp. 1-3.

(Continued)

*Primary Examiner* — Deborah D Carr
(74) *Attorney, Agent, or Firm* — Lerner David LLP

(57) ABSTRACT

The present disclosure relates to a method for preparing acrylic acid, and more particularly, to a method for preparing acrylic acid by dehydrating a lactic acid molecule through different steps with different temperatures. According to the preparation method of the present disclosure, acrylic acid can be prepared from lactic acid with a high conversion rate and yield, and also energy consumption can be further reduced as compared with a conventional method.

12 Claims, No Drawings

(56) References Cited

FOREIGN PATENT DOCUMENTS

| | | | |
|---|---|---|---|
| KR | 101033660 | B1 | 5/2011 |
| KR | 101093819 | B1 | 12/2011 |
| KR | 101187804 | B1 | 10/2012 |
| WO | 2012156921 | A1 | 11/2012 |
| WO | 2013155297 | A2 | 10/2013 |
| WO | 2015016217 | A1 | 2/2015 |

OTHER PUBLICATIONS

Buitelaar, M. M. et al., "Process Designs for Converting Propylene Glycol to Acrylic Acid via Lactic Acid and Allyl Alcohol" I & EC research, ACS Publications, Dec. 2019, pp. 1183-1192, vol. 59, Issue 3.

* cited by examiner

METHOD FOR PREPARING AN ACRYLIC ACID

CROSS-REFERENCE TO RELATED APPLICATION(S)

The present application is a national stage entry under 35 U.S.C. § 371 of International Application No. PCT/KR2021/016059 filed on Nov. 5, 2021, which claims priority from Korean Patent Applications No. 10-2020-0150320 filed on Nov. 11, 2020 and No. 10-2021-0150793 filed on Nov. 4, 2021, all the disclosures of which are incorporated herein by reference.

TECHNICAL FIELD

The present disclosure relates to a method for preparing acrylic acid, and more particularly, to a method for preparing acrylic acid by dehydrating a lactic acid molecule.

BACKGROUND ART

Acrylic acid is an organic compound having both a carboxylic acid and an unsaturated double bond in a molecule, is very simple in its structure and can be polymerized while being converted into various materials, and thus is used in various industrial fields.

Specifically, acrylic acid is used as polyacrylic acid, dots, adhesives, paints, etc. required for the production of a superabsorbent polymer, or can be used as a raw material for preparing other types of acrylate-based monomers, or may be used as a raw material for polymerizing with various other monomers such as acrylamide, acrylonitrile, styrene, and alpha olefin.

Such acrylic acid is generally prepared using propylene produced in the process of refining and separating a crude oil, such as naphtha cracking.

However, recently, as high attention is focused on crude oil depletion and environmental problems, interest in a method for preparing acrylic acid using an eco-friendly raw material is growing.

DETAILED DESCRIPTION OF THE INVENTION

Technical Problem

It is one object of the present disclosure to provide a method capable of preparing acrylic acid from lactic acid with high conversion rate and yield.

Technical Solution

Provided herein is a method for preparing acrylic acid, comprising the steps of: a first step of supplying an aqueous lactic acid solution to a reactor using a carrier gas; a second step of vaporizing the aqueous lactic acid solution; a third step of bringing the vaporized lactic acid molecule into contact with a dehydration catalyst; and a fourth step of obtaining acrylic acid, wherein the temperatures of the second to fourth steps are each independently adjusted.

According to an embodiment of the present disclosure, the second step may be performed under a temperature condition of about 200° C. to about 290° C., preferably under a temperature condition of about 200° C. or more, or about 230° C. or more, or about 250° C. or more and about 290° C. or less, or about 270° C. or less, or about 260° C.

Further, the second step may be performed in the presence of quartz.

According to another embodiment of the present disclosure, the third step may be performed under a temperature condition of more than 350° C. and about 400° C. or less, preferably under a temperature condition of more 350° C., or about 355° C. or more, or about 360° C. or more, and about 400° C. or less, or about 390° C. or less, or about 380° C. or less.

Further, the dehydration catalyst may include at least one selected from the group consisting of a calcium phosphate-based catalyst, a sodium phosphate-based catalyst, and an aluminum phosphate-based catalyst.

According to another embodiment of the present disclosure, in the first step, the aqueous lactic acid solution may be supplied at a flow rate of about 0.01 to about 10/hour, or at a flow rate of about 0.1 to about 5/hour, or about 0.1 to about 1/hour, based on a supply weight of lactic acid relative to a weight of the catalyst.

In this case, a concentration of the aqueous lactic acid solution in the first step may be about 10 to about 80 wt %.

According to another aspect of the present disclosure, the first to fourth steps are performed using a reactor equipped with a single reaction tube and a heating unit; the single reaction tube comprises a supply unit to which an aqueous lactic acid solution is supplied, a vaporization unit that vaporizes the aqueous lactic acid solution, a catalyst unit that brings the vaporized lactic acid molecule into contact with a dehydration catalyst; and a discharge unit that discharges acrylic acid; the heating unit comprises a first heating unit that heats the vaporization unit in a shape wrapping the single reaction tube, a second heating unit that is discontinuous with the first heating unit and heats a boundary portion between the vaporization unit and the catalyst unit and a front end of the catalyst unit, and a third heating unit this is discontinuous with the second heating unit and heats the rear end of the catalyst unit, and the temperatures of the second to fourth steps are each independently adjusted by the heating unit.

In this case, the first heating unit may be heated so that the inside of the vaporization unit of the single reaction tube is maintained at a temperature condition of about 200° C. to about 290° C. This is a temperature condition of the second step described above, and specifically may refer to a temperature condition of about 200° C. to about 290° C., preferably a temperature condition of about 200° C. or more, or about 230° C. or more, or about 250° C. or more and about 290° C. or less, or about 270° C. or less, or about 260° C.

Further, the second heating unit and the third heating unit may be heated so that the inside of the catalyst unit of the single reaction tube is maintained at a temperature condition of more than 350° C. and about 400° C. or less. This is a temperature condition of the third step described above, and specifically may refer to a temperature condition of about more than 350° C. and about 400° C. or less, preferably a temperature condition of more than 350° C., or about 355° C. or more, or about 360° C. or more, and about 400° C. or less, or about 390° C. or less, or about 380° C. or less.

In this case, a set temperature of the second heating unit may be higher than a set temperature of the third heating unit.

Specifically, a set temperature of the second heating unit may be about 15° C. to about 30° C. higher than a set temperature of the third heating unit.

As used herein, the terms “a first,” “a second,” etc. are used herein to explain various constitutional elements, and these terms are used only to distinguish one constitutional element from another constitutional element.

The technical terms used herein is only to explain exemplary embodiments and is not intended to limit the scope of the present disclosure.

The singular forms "a," "an" and "the" are intended to include plural forms, unless the context clearly indicates otherwise.

It should be understood that the terms "comprise," "include", "have", etc. are used herein to specify the presence of stated features, integers, steps, components or combinations thereof, but do not preclude the presence or addition of one or more other features, integers, steps, components, or combinations thereof.

Also, as used herein, in case a layer or an element is mentioned to be formed "on" or "above" layers or elements, it means that the layer or element is directly formed on the layers or elements, or it means that other layers or elements may be additionally formed between the layers, on a subject, or on a substrate.

Although the present disclosure may have various forms and various modifications may be made thereto, specific examples will be exemplified and explained in detail below. However, it is not intended to limit the present disclosure to specific disclosure, and it should be understood that the present disclosure includes all the modifications, equivalents or replacements thereof without departing from the spirit and technical scope of the present disclosure.

Now, the present disclosure will be described in more detail.

According to one aspect of the present disclosure, there is provided a method for preparing acrylic acid, comprising the steps of: a first step of supplying an aqueous lactic acid solution to a reactor using a carrier gas; a second step of vaporizing the aqueous lactic acid solution; a third step of bringing the vaporized lactic acid molecule into contact with a dehydration catalyst; and a fourth step of obtaining acrylic acid, wherein the temperatures of the second to fourth steps are each independently adjusted.

According to another aspect of the present disclosure, the first to fourth steps are performed using a reactor equipped with a single reaction tube and a heating unit; the single reaction tube comprises a supply unit to which an aqueous lactic acid solution is supplied, a vaporization unit that vaporizes the aqueous lactic acid solution, a catalyst unit that brings the vaporized lactic acid molecule into contact with a dehydration catalyst; and a discharge unit that discharges acrylic acid; the heating unit comprises a first heating unit that heats the vaporization unit in a shape wrapping the single reaction tube, a second heating unit that is discontinuous with the first heating unit and heats a boundary portion between the vaporization unit and the catalyst unit and a front end of the catalyst unit, and a third heating unit this is discontinuous with the second heating unit and heats the rear end of the catalyst unit, and the temperatures of the second to fourth steps are each independently adjusted by the heating unit.

The present inventors have found that in a series of reactions to obtain acrylic acid by subjecting vaporized lactic acid molecules to a dehydration reaction in the presence of a catalyst, when the temperature of each step is independently adjusted by subdividing the vaporization step and the dehydration step, the efficiency of the reaction can be increased while reducing the generation of by-products, and the yield of acrylic acid and the conversion rate of lactic acid can be dramatically improved, thereby completing the present disclosure.

The dehydration reaction that proceeds for the vaporized lactic acid molecule in the presence of a catalyst can be represented by the following reaction mechanism.

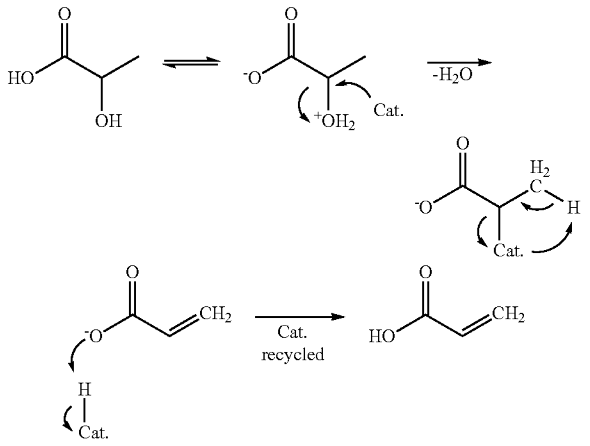

That is, the dehydration reaction of the lactic acid molecule can be explained as follows. A hydroxyl group linked to a carbonyl alpha position of the lactic acid molecule is released by a catalyst, hydrogen linked to a carbonyl beta position is also removed by a catalyst to form an acrylic acid anion, and then the hydrogen of the catalyst is linked to a carboxylate anion of acrylic acid to form acrylic acid.

It is known that such a reaction proceeds well for vaporized lactic acid molecules in the presence of a catalyst, but it competes with reactions that form by-products other than acrylic acid, such as i) an aldehyde formation reaction by decarboxylation or decarbonylation, ii) a propanoic acid formation reaction by reduction of acrylic acid, iii) a pentanedione formation reaction by condensation, and iv) an auto-esterification by dimerization, and the like, and therefore, the reaction conditions thereof need to be finely adjusted.

First, the reactants in the first step, i.e., lactic acid supplied as a feed, are in the form of an aqueous lactic acid solution, which may preferably be in a concentration range of about 10 to about 80 wt %.

When the concentration of lactic acid is too low, there is a problem that the efficiency of the vaporization reaction in the vaporization step and the efficiency of a subsequent lactic acid dehydration reaction become too low. When the concentration of lactic acid is too high, the content of oligomers such as dimers in the aqueous lactic acid solution increases and thus the efficiency of the lactic acid dehydration reaction of by-products may be lowered, which may cause a problem that the production of by-products is promoted.

And, in the first step, the aqueous lactic acid solution may be supplied at a flow rate of about 0.01 to about 10/hour, or 0.1 to about 5/hour, or about 0.1 to about 1/hour, based on the supply weight of lactic acid relative to the weight of the catalyst.

When the supply amount of an aqueous lactic acid solution is too small, the residence time of lactic acid at high temperature increases, the rate of loss due to thermal decomposition increases. In addition, there may be a problem in that other side reactions increase. When the supply amount of an aqueous lactic acid solution is too large, lactic acid is not sufficiently vaporized by a heat source, and the temperature of the vaporization unit and the upper end of a catalyst layer is lowered, which may cause a problem that catalyst performance is deteriorated.

And, lactic acid supplied as a feed may be supplied by a carrier gas. As the carrier gas used at this time, an inert gas that does not affect the vaporization reaction or the dehydration reaction, such as nitrogen or a group 18 gas, can be used.

The flow rate of the carrier gas used for the reaction may be about 1 to about 1000 times, or about 10 to about 500 times, or about 20 to about 300 times the supply amount of the aqueous lactic acid solution.

According to an embodiment of the present disclosure, the second step, that is, the vaporization reaction of lactic acid molecules, is performed under a temperature condition of about 200° C. to about 290° C., preferably under a temperature condition of about 200° C. or more, or about 230° C. or more, or about 250° C. or more and about 290° C. or less, or about 270° C. or less, or about 260° C.

When the temperature of the vaporization reaction is too low, the efficiency of the vaporization reaction is lowered, which may lead to a problem that the efficiency of a subsequent dehydration reaction is also lowered, and when the temperature of the vaporization reaction is too high, decarboxylation or decarbonylation proceeds more remarkably in the vaporized lactic acid molecule, which may cause a problem that production of aldehyde is promoted.

Further, the second step may be performed in the presence of quartz. Specifically, the quartz may be in the form of quartz wool with a large surface area, or quartz particle.

That is, the lactic acid molecule supplied to the supply unit may be adsorbed onto the surface of the quartz wool or the like in the vaporization unit inside the reactor according to the flow of the carrier gas, and in this state, it may receive supply of heat from the quartz wool or the like to be vaporized.

And, as described above, the reactor used for this reaction may be provided with a single reaction tube and a heating unit, and the heating unit may be a shape wrapping the single reaction tube. In this case, the first heating unit for heating the vaporization unit may be heated so that the inside of the vaporization part of the single reaction tube is maintained at a temperature condition of about 200° C. to about 290° C. This is the temperature condition of the second step described above, and specifically may refer to a temperature condition of about 200° C. to about 290° C., preferably about 200° C. or more, or about 230° C. or more, or about 250° C. or more and about 290° C. or less, or about 270° C. or less, or about 260° C.

However, throughout the specification, a temperature as a reaction condition of each reaction and a set temperature of the first to third heating units positioned at each site of the reactor may be different from each other. Specifically, the set temperature of the first to third heating units may be preferably set higher than the temperature of the respective corresponding reaction conditions. This may be because external gas and reactants are continuously supplied into a reactor according to the flow of the carrier gas, particularly, the temperature of the reactants supplied to the supply unit is commonly lower than the temperature of the vaporization unit, and in the vaporization unit, the temperature is continuously lowered due to the vaporization of lactic acid and water. Moreover, the temperature of the vaporization unit where the vaporization reaction proceeds is lower than the temperature of the catalyst unit where the dehydration reaction proceeds.

From this viewpoint, the first heating unit may be preferably set to a target temperature of the vaporization unit, that is, about 15 to about 30° C. higher than the preferred temperature of the above-mentioned vaporization reaction.

Then, the gaseous reaction product containing the vaporized lactic acid single molecule continues to move to a catalyst unit where the catalyst exists according to the flow of the carrier gas, and can be charged into a dehydration reaction, that is, the third step.

According to another embodiment of the present disclosure, the third step is performed under a temperature condition of more than 350° C. and about 400° C. or less, preferably under a temperature condition of more than 350° C., or about 355° C. or more, or about 360° C. or more, and about 400° C. or less, or about 390° C. or less, or about 380° C. or less.

When the temperature of the third step is too low, there may be a problem that the lactic acid conversion rate and the acrylic acid yield are greatly reduced, and when the temperature in step 3 is too high, i) an aldehyde formation reaction by decarboxylation or decarbonylation reaction, ii) a propanoic acid formation reaction by reduction of acrylic acid, iii) a pentanedione formation reaction by condensation, and the like are more promoted, which may cause a problem that by-products are increased.

And, as described above, the temperature of the catalyst unit as the dehydration reaction condition and the set temperature of the second and third heating units positioned at each site of the reactor may be different from each other.

Specifically, the second heating unit may be in the shape wrapping, in the interior of the reactor, i) a boundary portion between the vaporization unit and the catalyst unit and ii) a portion corresponding thereto in a single reaction tube for heating the front end of the catalyst unit. The third heating unit may be in the shape wrapping iii) a portion corresponding thereto in a single reaction tube for heating the rear end of the catalyst unit.

In addition, the second heating unit and the third heating unit may be heated so that the inside of the catalyst unit of the single reaction tube is maintained at a temperature of more than 350° C. and about 400° C. or less. This is the temperature condition of the third step described above, and may refer to a temperature condition of more than 350° C. and about 400° C. or less, preferably a temperature condition of more than 350° C., or about 355° C. or more, or about 360° C. or more, and about 400° C. or less, or about 390° C. or less, or about 380° C. or less.

In this case, it may be preferable that the set temperature of the second heating unit is higher than the set temperature of the third heating unit, specifically, it may be preferable that the set temperature of the second heating unit is about 15° C. to about 30° C. higher than the set temperature of the third heating unit.

For example, it may be preferable that the second and third heating units are set higher than the target temperature of the catalyst unit, that is, about 15° C. to about 30° C. higher than the above-mentioned preferable temperature for the dehydration reaction. In particular, the second heating unit may be set to a higher temperature than the third heating unit, and for example, it may be set to about 15° C. to about 30° C. higher temperature.

As described above, due to the type of reaction in which external gas and reactants are continuously supplied into the reactor according to the flow of the carrier gas, the temperature at the front end of the vaporization unit and the catalyst unit is inevitably lowered continuously. This is because the temperature of the vaporization unit and the front end of the catalyst unit may be lowered, thereby greatly reducing the overall reaction efficiency.

In the conventional case, in order to prevent these problems, a method such as setting the overall temperature of the reactor higher or preheating the reactor before the reaction proceeds to reach a target temperature, and then charging to the reaction was used. However, in such a case, energy is wasted unnecessarily, and the efficiency of the reaction may be lowered due to the side reaction described above under high temperature conditions, whereas it is still difficult to solve the problem that the temperature at the front end of the catalyst unit is lowered.

In the case of the present disclosure, the temperature of the vaporization unit, the boundary portion between the vaporization unit and the catalyst unit, the front end of the catalyst unit, and the rear end of the catalyst unit are set differently according to the needs of each reaction. In particular, a separate heating unit, that is, a second heating unit, capable of supplying heat is positioned at the boundary portion between the vaporization unit and the catalyst unit, where the temperature condition changes rapidly, whereby the energy efficiency can be further increased and also the reaction efficiency can be improved.

In addition, the dehydration catalyst may include at least one selected from the group consisting of a calcium phosphate-based catalyst, a sodium phosphate-based catalyst, and an aluminum phosphate-based catalyst, and other reaction conditions can be used without any particular limitation as long as they are those generally used in the art to which the present disclosure pertains, and are not contrary to the content defined herein.

More specifically, the dehydration catalyst may include $CaSO_4/Na_2SO_4$; $Na_4P_2O_7/CaSO_4$; $Na_4P_2O_7/Ca_3(PO_4)_2$; $NaH_2PO_4$—$NaHCO_3/SiO_2$; $AlPO_4$—$NH_3$; $Ca_3(PO_4)_2/CaSO_4$; $Ca_2P_2O_7$; $Ca_5(PO_4)_3(OH)$ and the like.

Advantageous Effects

According to the preparation method of the present disclosure, acrylic acid can be prepared from lactic acid with a high conversion rate and yield, and also energy consumption can be further reduced as compared with a conventional method.

DETAILED DESCRIPTION OF THE EMBODIMENTS

Hereinafter, the action and effect of the invention will be described in more detail with reference to specific examples of the invention. However, these examples are presented for illustrative purposes only and the scope of the invention is not limited thereby in any way.

Example

A reaction cylinder made of quartz with an inner diameter of ⅞ inches and a length of 860 mm was prepared as a single reaction tube.

A non-reactive glass tube and quartz wool were added so that quartz sand is not poured down in a region of about 150 mm to about 300 mm from the upper end of the single reaction tube, and quartz sand was filled therein to form a vaporization unit.

As the catalyst, a catalyst obtained by molding a calcium phosphate catalyst into a cylindrical pellet having a diameter of about 3 mm and a length of about 3 mm was used.

Then, a non-reactive glass tube and quartz wool were placed in a region of a length of about 300 mm from the lower end of the vaporized portion so that the catalyst was not poured down, and about 50 g of the catalyst was filled therein to form a catalyst unit.

A first heating unit having a length of about 200 mm was provided in a shape surrounding the entire region corresponding to the vaporization unit of the single reaction tube, from a position of about 100 mm downward from the top of the single reaction tube.

Alternatively, a second heating unit having a length of about 100 mm was provided in a shape surrounding a boundary portion between the vaporization unit and the catalyst unit of a single reaction tube, and a region corresponding to the front end of the catalyst unit, from the rear end of the first heating unit.

Alternatively, a third heating unit having a length of about 200 mm was provided in a shape surrounding a region corresponding to the rear end of the catalyst unit of the single reaction tube from the rear end of the second heating unit.

Alternatively, a fourth heating unit having a length of about 200 mm was provided in a shape surrounding a region corresponding to a discharge unit of the single reaction tube from the rear end of the second heating unit.

A thermocouple was provided at the front and rear ends of the catalyst unit of the single reaction tube so as to measure the internal temperature.

Nitrogen was used as a carrier gas, the flow rate was about 80 ml/min, and an aqueous lactic acid solution having a concentration of about 40 wt % was set at a flow rate of about 0.4 ml/min, and supplied to the reactor. The density of the supplied aqueous lactic acid solution was about 1.08 g/ml, the supply rate of the aqueous lactic acid solution was about 10.37 g/hour based on the amount of lactic acid, and it was calculated to be about 0.21/hour for the reference weight (1 g) of the supplied catalyst (50 g).

The product sample obtained from the discharge unit was collected, cooled to about 4° C. in a condenser, and collected in the liquid phase, and the amount of acrylic acid obtained was confirmed by HPLC.

During the reaction, the set temperatures of the first to fourth heating units were made respectively different from each other, and the temperatures of the front and rear ends of the catalyst unit were measured while performing the vaporization reaction and the dehydration reaction.

The measurement results are summarized in Table below.

TABLE 1

| | Temperature | | | | |
|---|---|---|---|---|---|
| | Set temperature for each region (1st, 2nd, 3rd, 4th heating unit) | Temperature of the front and rear ends of catalyst unit | Lactic acid conversion rate (%) | Acrylic acid yield (%) | Acetaldehyde yield (%) |
| Reference Example 1 | 250, 320, 350, 350 | 298, 349 | 47.7 | 14.2 | 15.3 |
| Reference Example 2 | 250, 330, 350, 350 | 317, 361 | 58.7 | 20.3 | 16.9 |
| Reference Example 3 | 250, 340, 350, 350 | 335, 364 | 76.9 | 22.3 | 18.1 |
| Comparative Example 1 | 300, 340, 350, 350 | 367, 370 | 97.0 | 29.1 | 30.8 |
| Comparative Example 2 | 350, 330, 350, 350 | 375, 370 | 100 | 25.7 | 40.0 |
| Example 1 | 250, 370, 350, 350 | 366, 370 | 92.6 | 40.1 | 19.2 |
| Example 2 | 250, 375, 350, 350 | 370, 370 | 94.0 | 48.1 | 20.9 |

Referring to Table 1, it can be clearly confirmed that the method for preparing acrylic acid according to an embodiment of the present disclosure can prepare acrylic acid from lactic acid with a high conversion rate and a high yield.

Further, it can be confirmed that when the temperature of the first heating unit (lactic acid vaporization, second stage) increases to 300° C. or more as in Comparative Examples 1 and 2, the rate at which acetaldehyde is formed is higher than in Examples 1 and 2 even though the temperature of the front end of the catalyst unit was set similarly to Examples 1 and 2. This seems to be due to the fact that the temperature of lactic acid vaporization is too high, so that the decarboxylation reaction or decarbonylation reaction is more predominant than the dehydration reaction.

Comparing the results according to Examples and Comparative Examples, it can be confirmed that when the temperature of each step of the lactic acid vaporization reaction, such as a step of supplying an aqueous lactic acid solution to a reactor using a carrier gas, a step of vaporizing the aqueous lactic acid solution, a step of bring the vaporized lactic acid molecule into contact with a dehydration catalyst, and a step of obtaining acrylic acid, and the like as in an embodiment of the present disclosure is adjusted independently, side reactions such as acetaldehyde generation can be effectively suppressed while maximizing lactic acid conversion rate and acrylic acid yield.

The invention claimed is:

1. A method for preparing acrylic acid, comprising the steps of:

a first step of supplying an aqueous lactic acid solution to a reactor using a carrier gas;

a second step of vaporizing the aqueous lactic acid solution to obtain vaporized lactic acid;

a third step of bringing the vaporized lactic acid into contact with a dehydration catalyst; and a fourth step of obtaining acrylic acid, wherein;

the first to the fourth steps are performed using a reactor equipped with a single reaction tube and a heating unit;

the single reaction tube comprises a supply unit to which the aqueous lactic acid solution is supplied, a vaporization unit that vaporizes the aqueous lactic acid solution, a catalyst unit that brings the vaporized lactic acid into contact with the dehydration catalyst; and a discharge unit that discharges the acrylic acid;

a heating unit comprises a first heating unit that heats the vaporization unit in a shape wrapping the single reaction tube, a second heating unit that is discontinuous with the first heating unit and heats a boundary portion between the vaporization unit and the catalyst unit and a front end of the catalyst unit, and a third heating unit which is discontinuous with the second heating unit and heats the rear end of the catalyst unit; and temperatures of the second to the fourth steps are each independently adjusted by the heating unit; and a set temperature of the second heating unit is higher than a set temperature of the third heating unit.

2. The method for preparing acrylic acid according to claim 1, wherein:

the second step is performed under a temperature of 200° C. to 290° C.

3. The method for preparing acrylic acid according to claim 1, wherein:

the second step is performed in the presence of quartz.

4. The method for preparing acrylic acid according to claim 1, wherein:

the third step is performed under a temperature of more than 350° C. and 400° C. or less.

5. The method for preparing acrylic acid according to claim 1, wherein:

the dehydration catalyst comprises at least one selected from a calcium phosphate-based catalyst, a sodium phosphate-based catalyst, or an aluminum phosphate-based catalyst.

6. The method for preparing acrylic acid according to claim 1, wherein:

in the first step, the aqueous lactic acid solution is supplied at a flow rate of 0.01 to 10/hour, based on a supply weight of lactic acid relative to a weight of the dehydration catalyst.

7. The method for preparing acrylic acid according to claim 1, wherein:

a concentration of the aqueous lactic acid solution in the first step is 10 to 80 wt %.

8. The method for preparing acrylic acid according to claim 1, wherein:

the first heating unit is heated so that the inside of the vaporization unit of the single reaction tube is maintained at a temperature condition of 200° C. to 290° C.

9. The method for preparing acrylic acid according to claim 1, wherein:

the second heating unit and the third heating unit are heated so that the inside of the vaporization unit of the single reaction tube is maintained at a temperature condition of more than 350° C. and 400° C. or less.

10. The method for preparing acrylic acid according to claim 1, wherein:

the set temperature of the second heating unit is 15° C. to 30° C. higher than the set temperature of the third heating unit.

11. The method for preparing acrylic acid according to claim 1, wherein:

a flow rate of the carrier gas is about 1 to about 1000 times a supply amount of the aqueous lactic acid solution.

12. The method for preparing acrylic acid according to claim 1, wherein:

the dehydration catalyst comprises $CaSO_4/Na_2SO_4$; $Na_4P_2O_7/CaSO_4$; $Na_4P_2O_7/Ca_3(PO_4)_2$; $NaH_2PO_4$—$NaHCO_3/SiO_2$; $AlPO_4$—$NH_3$; $Ca_3(PO_4)_2/CaSO_4$; $Ca_2P_2O_7$; or $Ca_5(PO_4)_3(OH)$.

* * * * *